(12) United States Patent
Sakai et al.

(10) Patent No.: US 7,975,524 B2
(45) Date of Patent: Jul. 12, 2011

(54) OXYGEN SENSOR INSPECTION METHOD AND APPARATUS AND OXYGEN SENSOR PRODUCTION METHOD

(75) Inventors: Shoichi Sakai, Midori (JP); Masami Kawashima, Gunma (JP)

(73) Assignee: Hitachi, Ltd., Tokyo (JP)

( * ) Notice: Subject to any disclaimer, the term of this patent is extended or adjusted under 35 U.S.C. 154(b) by 457 days.

(21) Appl. No.: 12/248,062

(22) Filed: Oct. 9, 2008

(65) Prior Publication Data
US 2009/0095048 A1    Apr. 16, 2009

(30) Foreign Application Priority Data

Oct. 12, 2007 (JP) .................. 2007-266462

(51) Int. Cl.
*G01N 21/00* (2006.01)
(52) U.S. Cl. ......................................... 73/1.06
(58) Field of Classification Search ..................... 73/1.06
See application file for complete search history.

(56) References Cited

U.S. PATENT DOCUMENTS

| | | | | |
|---|---|---|---|---|
| 6,629,444 B2 * | 10/2003 | Peng | ............... | 73/1.06 |
| 7,013,701 B2 * | 3/2006 | Kawashima | ............... | 73/1.06 |
| 7,251,981 B2 * | 8/2007 | Sasaki et al. | ............... | 73/23.21 |
| 2004/0123642 A1 * | 7/2004 | Kawashima | ............... | 73/1.06 |
| 2005/0155405 A1 * | 7/2005 | Sasaki et al. | ............... | 73/1.06 |
| 2005/0158459 A1 | 7/2005 | Sakai et al. | | |

FOREIGN PATENT DOCUMENTS

JP    2005-201840    7/2005

* cited by examiner

*Primary Examiner* — Hezron Williams
*Assistant Examiner* — Rodney T Frank
(74) *Attorney, Agent, or Firm* — Antonelli, Terry, Stout & Kraus, LLP.

(57) ABSTRACT

There is provided an inspection method of an oxygen sensor, which includes a sensing portion having a reference electrode, a sensing electrode and an oxygen ion conducting solid electrolyte layer arranged between the reference electrode and the sensing electrode. The inspection method contains the steps of reading a first output value of the oxygen sensor under a condition that the sensing portion of the oxygen sensor is subjected to a first inspection gas and then a second output value of the oxygen sensor under a condition that the sensing portion of the oxygen sensor is subjected to a second inspection gas different in oxygen concentration from the first inspection gas and judging the oxygen sensor to be defective or nondefective based on the first and second output values.

7 Claims, 4 Drawing Sheets

OXYGEN SENSOR INSPECTION METHOD AND APPARATUS AND OXYGEN SENSOR PRODUCTION METHOD

BACKGROUND OF THE INVENTION

The present invention relates to an oxygen sensor for detecting the concentration of oxygen in gas under measurement (such as automotive engine exhaust gas) and, more particularly, to a method and apparatus for quality inspection of the oxygen sensor and a method for production of the oxygen sensor.

Japanese Laid-Open Patent Publication No. 2005-201840 discloses an oxygen sensor that includes a substrate portion, a sensing portion disposed on the substrate portion and having an oxygen ion conducting solid electrolyte layer and a pair of inner and outer electrodes on opposite sides of the solid electrolyte layer and a protector fixed to the substrate portion so as to surround therein the sensing portion. The sensing portion is generally prepared by printing the inner electrode on the substrate portion, printing the solid electrolyte layer on the inner electrode, printing the outer electrode on the solid electrolyte layer, and then, sintering the printed laminate of the solid electrolyte layer and inner and outer electrodes at temperatures of 1400 to 1500° C.

SUMMARY OF THE INVENTION

In the presence of a foreign substance or bubble in a boundary area between the solid electrolyte layer and the electrode, a stress concentration occurs at the boundary area due to shrinkage of the solid electrolyte layer during the high-temperature sintering process so that the sensing portion becomes cracked to cause a deterioration in sensor performance. For this reason, the sensing portion is visually inspected by liquid penetrant test (so-called red check test) before fixing the protector to the sensor substrate portion, in order to use the conforming (nondefective) sensing portion and reject the defective sensing portion. In such visual inspection test, however, there is a possibility of missing a small crack in the sensing portion.

It is accordingly an object of the present invention to provide a quality inspection accuracy improvement technique for a solid electrolyte type oxygen sensor.

According to a first aspect of the present invention, there is provided an inspection method of an oxygen sensor, the oxygen sensor comprising a sensing portion having a reference electrode, a sensing electrode and an oxygen ion conducting solid electrolyte layer arranged between the reference electrode and the sensing electrode, the inspection method comprising: reading a first output value of the oxygen sensor under a condition that the sensing portion of the oxygen sensor is subjected to a first inspection gas and then a second output value of the oxygen sensor under a condition that the sensing portion of the oxygen sensor is subjected to a second inspection gas, the first and second inspection gases having different oxygen concentrations from each other; and judging the oxygen sensor to be defective or nondefective based on the first and second output values.

According to a second aspect of the present invention, there is provided a production method of an oxygen sensor, the oxygen sensor comprising a substrate portion, a sensing portion disposed on the substrate portion and having a reference electrode, a sensing electrode and an oxygen ion conducting solid electrolyte layer arranged between the reference electrode and the sensing electrode and a protector covering therewith the sensing portion, the production method comprising: printing the reference electrode, the solid electrolyte layer and the sensing electrode successively on the substrate portion; sintering the printed reference electrode, solid electrolyte layer and sensing electrode to form the sensing portion on the substrate portion; after the sintering, fixing the protector to cover the sensing portion with the protector; after the fixing, reading a first output value of the oxygen sensor under a condition that the sensing portion of the oxygen sensor is subjected to a first inspection gas and then a second output value of the oxygen sensor under a condition that the sensing portion of the oxygen sensor is subjected to a second inspection gas, the first and second inspection gases having different oxygen concentrations from each other; and judging the oxygen sensor to be defective or nondefective based on the first and second output values.

According to a third aspect of the present invention, there is provided an inspection apparatus of an oxygen sensor, the oxygen sensor comprising a sensing portion having a reference electrode, a sensing electrode and an oxygen ion conducting solid electrolyte layer arranged between the reference electrode and the sensing electrode, the inspection apparatus comprising: a gas supply unit that supplies first and second inspection gases selectively to the sensing portion, the first and second inspection gases having different oxygen concentrations from each other; and a control unit that reads a first output value of the oxygen sensor under a condition that the sensing portion of the oxygen sensor is subjected to the first inspection gas and then a second output value of the oxygen sensor under a condition that the sensing portion of the oxygen sensor is subjected to the second inspection gas and judges the oxygen sensor to be defective or nondefective based on the first and second output values.

The other objects and features of the present invention will also become understood from the following description.

DESCRIPTIONS OF THE EMBODIMENTS

The present invention will be described in detail below with reference to the drawings.

The following embodiment provides an oxygen sensor inspection apparatus 1 for inspecting the quality of an oxygen sensor 50.

Figure 1:
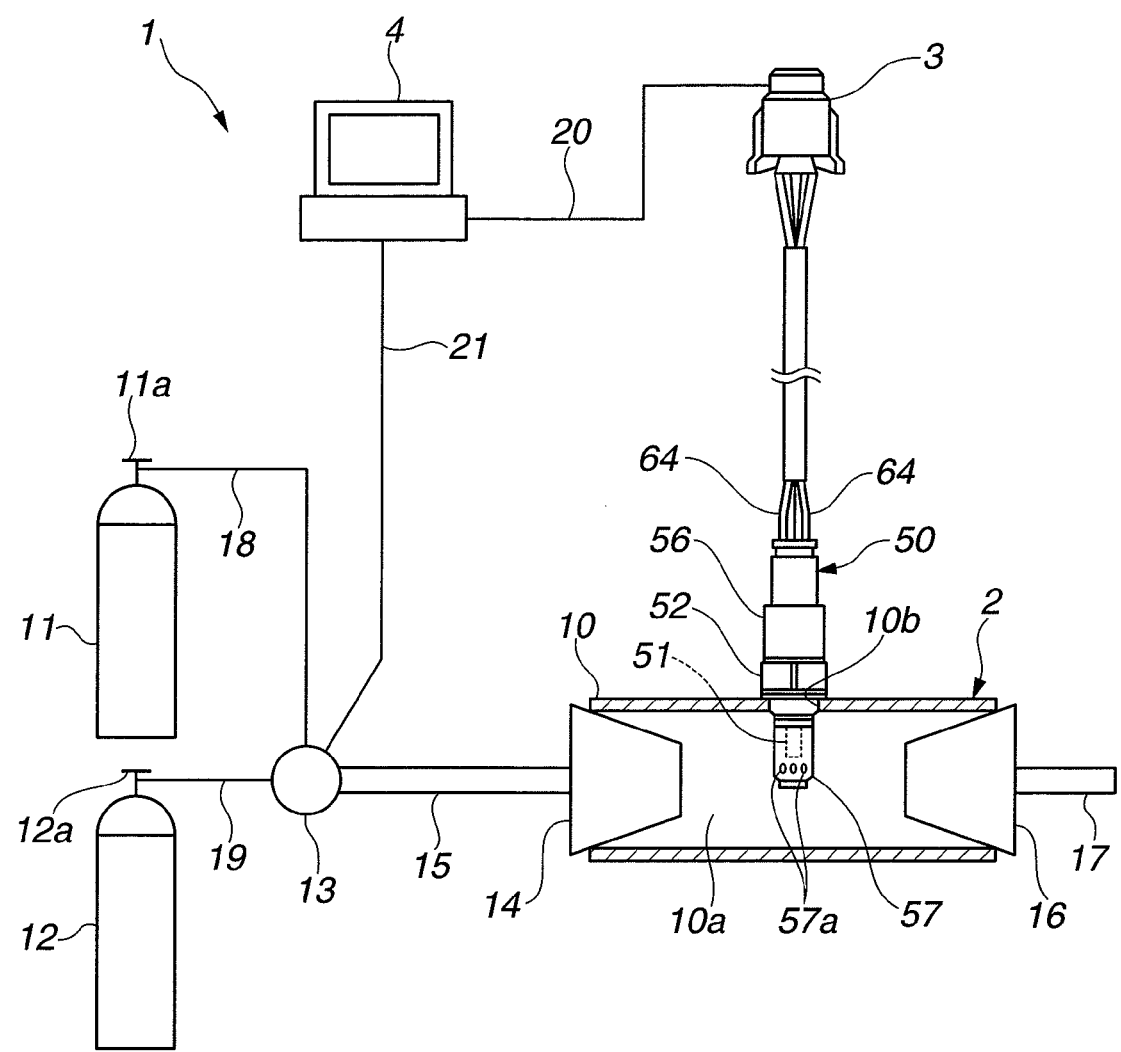
FIG. 1 is a schematic view of an oxygen sensor inspection apparatus according to one embodiment of the present invention.

As shown in FIG. 1, the oxygen sensor inspection apparatus 1 includes a gas supply unit 2 that supplies two kinds of inspection gases selectively to the oxygen sensor 50, a power supply unit 3 that energizes the oxygen sensor 50 and a control unit 4 that controls the operations of the gas supply unit 2 and the power supply unit 3.

The gas supply unit 2 has a sensor support 10 for supporting the oxygen sensor 50, first and second gas cylinders 11 and 12 for storing the first and second inspection gases, respectively, and a switching valve 13 for switching gas communications from the gas cylinders 11 and 12 to the oxygen sensor 50.

The sensor support 10 is formed into a cylindrical shape to define therein a gas chamber 10a. A screw hole 10b is cut in a cylindrical wall of the sensor support 10. The oxygen sensor 50 is secured gastightly in the screw hole 10b via a gasket 62 with a sensing portion 120 of the oxygen sensor 50 located in the gas chamber 10a and the other portion of the oxygen sensor 50 exposed to the outside of the sensor support 10. Opposite ends of the sensor support 10 are connected to first and second pipes 15 and 17 via first and second joints 14 and 16, respectively, so that the first and second pipes 15 are in communication with the gas chamber 10a.

The first and second gas cylinders 11 and 12 are filled with the first and second inspection gases and equipped with valves 11a and 12a so as to eject or cut off the first and second inspection gases from the first and second gas cylinders 11 and 12, respectively.

The first and second inspection gases have different oxygen concentrations and are compressed in the first and second gas cylinders 11 and 12. Preferably, the second inspection gas has a lower oxygen concentration than the oxygen concentration of the first inspection gas and inertness to oxygen. It is particularly preferable that the second inspection gas consists of a single gas component such as nitrogen gas or inert gas e.g. highly-inert argon, neon or helium gas. In this case, the oxygen concentration of the second inspection gas is zero and lower than the oxygen concentration of the first inspection gas. By way of example, the first and second inspection gases are atmospheric air (mixed gas containing oxygen gas and nitrogen gas as main components with small amounts of carbon dioxide, hydrogen etc.) and nitrogen gas, respectively, in the present embodiment.

The switching valve 13 is formed of e.g. a solenoid valve. An upstream side of the switching valve 13 is connected to the first and second gas cylinders 11 via third and fourth pipes 18 and 19, respectively, whereas a downstream side of the switching valve 13 is connected to the gas chamber 10a via the first pipe 15.

The power supply unit 3 is connected to the oxygen sensor 50 and has a power supply circuit for applying a voltage to the oxygen sensor 50 and a current detection circuit for detecting a current through the oxygen sensor 50.

The control unit 4 has a computer system composed of a CPU to perform various control and operation processes, a storage section including a ROM and a RAM and a communication section connected to the power supply unit 3 and the switching valve 13 via harnesses 20 and 21, respectively, so that the control unit 4 controls the operations of the power supply unit 3 and the switching valve 13 and enables signal transmissions to/from the oxygen sensor 50 through the power supply unit 3.

Figure 2:
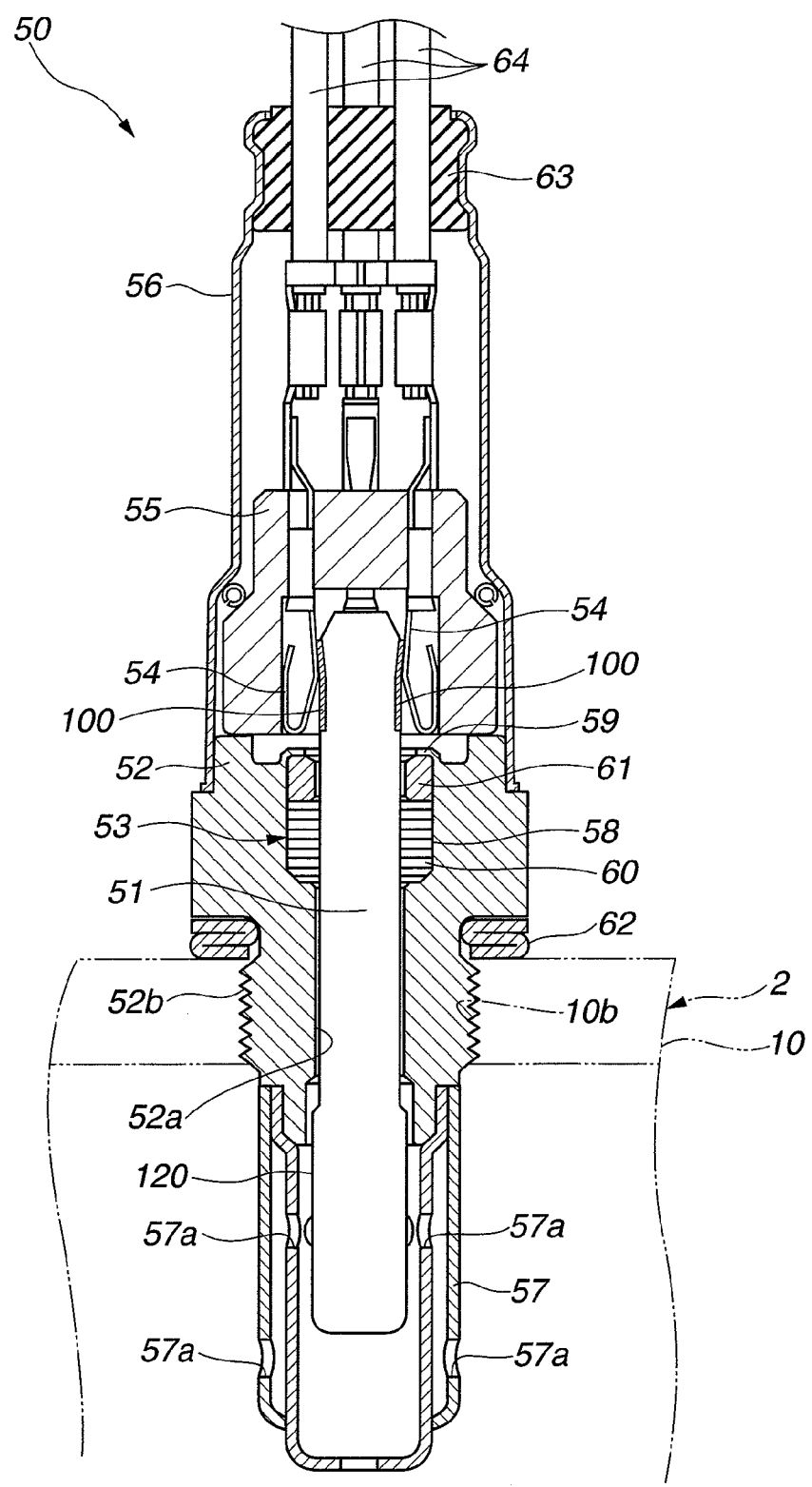
FIG. 2 is a section view of an oxygen sensor according to one embodiment of the present invention.

As shown in FIG. 2, the oxygen sensor 50 generally includes a sensor element 51, a holder 52, a positioning member 53, a terminal 54, a ceramic insulator 55, a casing 56, a protector 57, a seal member 63 and a harness 64. By way of example, the oxygen sensor 50 is designed for mounting on an exhaust pipe of a vehicle internal combustion engine to output an electrical signal responsive to the concentration of oxygen in exhaust gas from the engine in the present embodiment.

Figure 3:
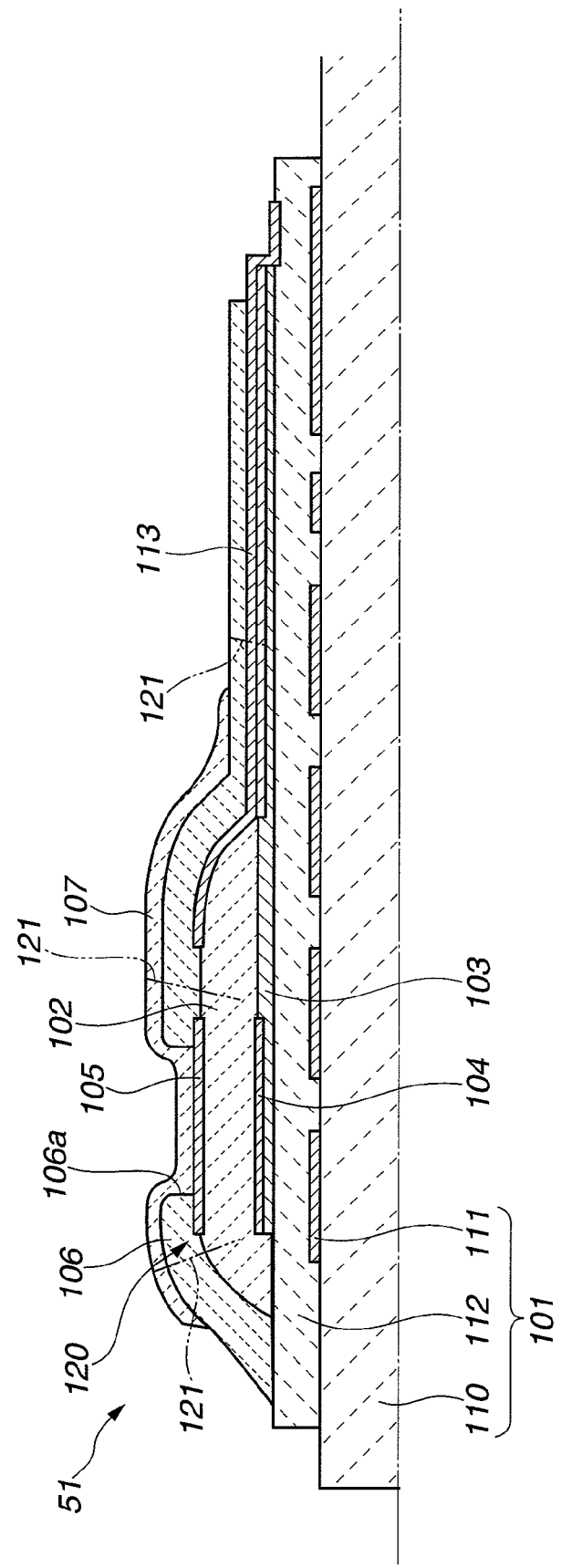
FIG. 3 is a section view of a sensing portion of the oxygen sensor according to one embodiment of the present invention.

The sensor element 51 has a column-shaped substrate portion 101, a sensing portion 120 disposed on a front end side of the substrate portion 101, an electrode pad 100 formed on a rear end side of the substrate portion 101 and leads 113 formed on the substrate portion 101 and connected between the sensing portion 120 and the electrode pad 100 as shown in FIG. 3.

The substrate portion 101 has a cylindrical solid core rod 110, a heater pattern 111 (as a heater) formed on an outer circumferential side of the core rod 110 and a heater insulation layer 112 formed on the outer circumferential side of the core rod 110 so as to cover the heater pattern 111 with the heater insulation layer 112.

The sensing portion 120 is located on a front end of the oxygen sensor 50 at a position corresponding to the heater pattern 111 and has a solid electrolyte layer 102, a porous layer 103, a reference electrode 104, a sensing electrode 105, a close-packed layer 106 and a protection layer 107.

The solid electrolyte layer 102 is formed of an oxygen ion conducting solid electrolyte material and arranged on the heater insulation layer 112.

The porous layer 103 is formed of an air-permeable material and also arranged on the heater insulation layer 112.

The reference electrode 104 and the sensing electrode 105 are formed of an electrically-conductive, oxygen-permeable material and arranged on inner and outer sides of the solid electrolyte layer 102, respectively. In other words, the solid electrolyte layer 102 is sandwiched between the reference electrode 104 and the sensing electrode 105. Each of the reference electrode 104 and the sensing electrode 105 is made integral with the corresponding lead 113. (In FIG. 3, the lead 113 integral with the electrode 104 is omitted for simplicity.)

The close-packed layer 106 is formed of an oxygen-impermeable material and arranged over the whole of the solid electrolyte layer 102 and the sensing electrode 105. An oxygen inlet port 106a is made in the close-packed layer 106 so that the central effective area of the sensing electrode 105 is exposed through the oxygen inlet port 106a.

The protection layer 107 is formed of an oxygen-permeable material that does not allow the passage of any poisoning gas in gas under measurement and is arranged over the close-packed layer 106 and the sensing electrode 105.

As the close-packed layer 106 and the protection layer 107 are exposed to the gas under measurement, oxygen in the gas under measurement is introduced to the sensing electrode 105 through the protection layer 107 and the oxygen inlet port 16a. By contrast, the reference electrode 104 is covered with the solid electrolyte layer 102 and thus is not directly exposed to the gas under measurement.

The holder 52 has an insertion hole 52a to hold therein the sensor element 51, with the electrode pad 100 of the sensor element 51 exposed at a rear end of the holder 52 (upper end in FIG. 2) and the sensing portion 120 of the sensor element 51 protruding from a front end of the holder 52 (bottom end in FIG. 2), and a screw thread 52b to be screwed into the screw hole 10b of the sensor support 10.

The positioning member 53 has an accommodation space 58 defined around the entire circumference of the sensor insertion hole 52a to accommodate therein a ceramic filler 60 and a spring spacer 61 and a swage portion 59 formed at an opening edge of the accommodation space 58. The ceramic filler 60 and the spacer 61 are a green talc powder and a ring washer, respectively, in the present embodiment. The swage portion 59 is formed by swaging to press the space 61 against the ceramic powder 60 and thereby compact the ceramic powder 60. With this, the positioning member 53 places the sensor element 51 in proper position in the holder 52 and maintains a gas seal between the sensor element 51 and the holder 52.

The terminal 54 is fixed by pressure welding to the electrode pad 100 of the sensor element 51 so as to take the output signal from the sensor element 51, The ceramic insulator 55 is fixed to the rear end of the holder 52 so as to hold therein the terminal 54.

The casing 56 is fixed to the rear end of the holder 52 so as to surround the ceramic insulator 55.

The protector 57 is fixed to the front end of the holder 52 by any appropriate process such as fitting, screw joining, adhesive bonding and laser welding so as to surround and cover therewith the sensing portion 120. In the present embodiment, the protector 57 has a bottomed-cylindrical double-walled structure as shown in FIG. 2. A plurality of vent holes 57a are formed in the protector 57 so that the gas under measurement is introduced to the sensing portion 120 through the vent holes 57a.

The seal member 63 is fitted in a rear open end of the casing 56 so that the rear end of the casing 56 is closed with the seal member 63.

The harness 64 is connected to the electrode pad 100 of the sensor element 51 through the terminal 54 and drawn out of the casing 56 through the seal member 63.

With the above structure, the oxygen sensor 50 carries out oxygen concentration measurements as follows.

When the heater pattern 111 generates heat by energization thereof, the generated heat is transferred to the sensing portion 120 through the heater insulation layer 112 to activate the solid electrolyte layer 102. The oxygen in the gas under measurement is introduced to the outer side of the solid electrolyte layer 102 through the protection layer 107, the oxygen inlet port 106a and the sensing electrode 105. On the other hand, the atmospheric air is introduced as a reference gas from a rear end of the oxygen sensor 50 to the inner side of the solid electrolyte layer 102 through the porous layer 103 and the reference electrode 104. In this state, the solid electrolyte layer 102 allows conduction of oxygen ions in response to the oxygen concentration difference between the inner and outer sides of the solid electrolyte layer 102. There arises an electromotive force between the reference electrode 105 and the sensing electrode 105 due to the oxygen ion conduction through the solid electrolyte layer 102. This electromotive force is outputted as the sensor output signal (voltage or current signal) through the leads 113, the electrode pad 100, the terminal 54 and the harness 64 so that the oxygen concentration of the gas under measurement is determined according to the sensor output signal.

The oxygen sensor 50 can be produced by the following procedure.

First, the cylindrical solid core rode 110 is formed by injection molding a ceramic material e.g. alumina.

The heater pattern 111 is next formed by curved-surface screen printing a heat generating material e.g. platinum or tungsten on the outer circumferential side of the core rod 110 while rotating the core rod 110.

The heater insulation layer 112 is then formed by curved-surface screen printing e.g. alumina on the outer circumferential side of the core rod 110 in such a manner that the heater pattern 111 is covered with the heater insulation layer 112.

The porous layer 103 is formed by curved-surface screen printing on the outer circumferential side of the core rod 110 in such a manner that the heater insulating layer 112 is covered with the porous layer 103.

The reference electrode 104 and the lead 113 are integrally formed by screen printing a conductive paste of e.g. platinum over the porous layer 103.

The solid electrolyte layer 102 is formed by curved-surface screen printing e.g. a paste of zirconia and yttria over the reference electrode 104 and the lead 113

The sensing electrode 105 and the lead 113 are integrally formed by screen printing a conductive paste of e.g. platinum over the solid electrolyte layer 102.

The close-packed layer 106 is formed by curved-surface screen printing a ceramic material e.g. alumina over the sensing electrode 105 and the solid electrolyte layer 102 in such a manner the effective area of the sensing electrode 105 is exposed through the oxygen inlet port 106a.

Subsequently, the protective layer 107 is formed by curved-surface screen printing e.g. a paste of alumina and magnesium oxide over the sensing electrode 105, the solid electrolyte layer 102 and the heater insulation layer 112 around the entire circumference of the core rod 110.

After the completion of the above printing process, the thus-obtained cylindrical workpiece including the solid electrolyte layer 102, the electrodes 104 and 105 is sintered at high temperature and thereby integrated into the sensor element 51.

The sensor element 51 and the other sensor components are assembled together by connecting the harness 64 with the leads 113 through the electrode pad 100 and the terminal 54, attaching the sensor element 51 to the sensor holder 52, fixing the casing 56 to the holder 52 and then fixing the protector 57 to the holder 52. By this, the oxygen sensor 50 is completed.

There may be a case where a crack 121 (as a defect) occurs in the sensor element 51, as indicated by a double-dashed line in FIG. 3, during the sintering and assembling processes although the frequency of occurrence of the crack 121 is low.

After the final assembly, the oxygen sensor 50 is inspected for the occurrence of such a crack 121 by means of the oxygen sensor inspection apparatus 1. To make a quality inspection test on the oxygen sensor 50, the oxygen sensor 50 is mounted on the sensor support 10 of the oxygen sensor inspection apparatus 1 by screwing the screw thread 52b into the thread hole 10b and connected to the power supply unit 3 of the oxygen sensor inspection apparatus 1. The quality inspection test is made under the conditions that the oxygen sensor 50 is energized to activate the sensor element 51 (solid electrolyte layer 102) by heat generation of the heating pattern 111 and that the valves 11a and 12a of the gas cylinders 11 and 12 are opened.

The quality inspection test of the oxygen sensor inspection apparatus 1 is based on the following principles.

Under the application of an inspection voltage between the reference electrode 104 and the sensing electrode 105 to allow oxygen ion conduction from the reference electrode 104 to the sensing electrode 105 through the solid electrolyte layer 102, the amount of oxygen ions conducted from the reference electrode 104 to the sensing electrode 105 depends on the oxygen concentration of the reference electrode 104. More specifically, the amount of oxygen ions conducted from the reference electrode 104 to the sensing electrode 105 decreases with the oxygen concentration of the reference electrode 104.

Figure 4:
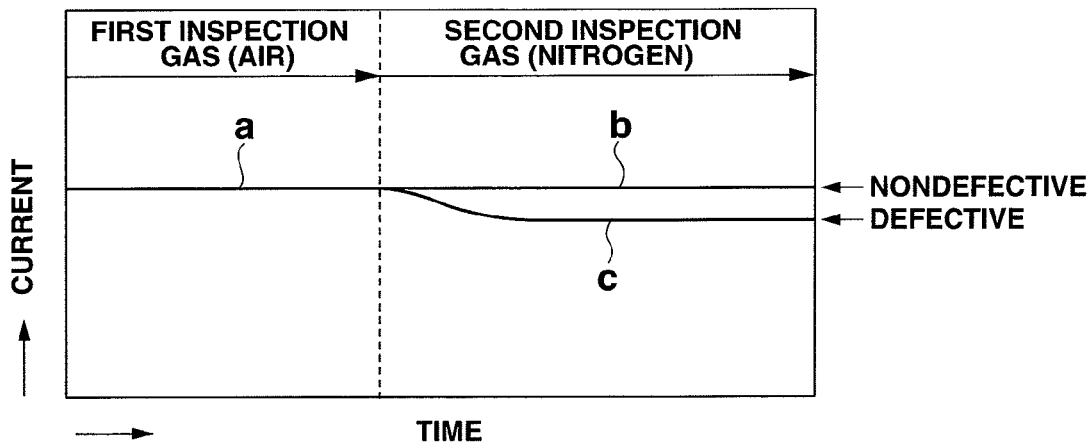
FIG. 4 is a graph showing the output characteristics of the oxygen sensor, when exposed to two kinds of inspection gases, according to one embodiment of the present invention.

In the occurrence of no crack in the sensing portion 102 of the oxygen sensor 50, there is no difference in the oxygen concentration of the reference electrode 104 and, by extension, the amount of oxygen ions conducted from the reference electrode 104 to the sensing electrode 105, between the conditions that the sensing electrode 102 is exposed to the first inspection gas (atmospheric air) and that the sensing electrode 102 is exposed to the second inspection gas (nitrogen gas). As shown in FIG. 4, the output current value of the oxygen sensor 50 in the atmosphere of the first inspection gas (indicated by line a) is the same as the output current value of the oxygen sensor 50 in the atmosphere of the second inspection gas (indicated by line b).

In the occurrence of the crack 121 in the sensing portion 120 of the sensor element 51, by contrast, the gas under measurement comes in the sensing portion 120 through the crack 121 and reaches the reference electrode 104 so that the oxygen concentration of the reference electrode 104 varies with the oxygen concentration of the gas under measurement. As the atmospheric air is used as the first inspection gas and the reference gas in the present embodiment, the oxygen concentration of the reference electrode 104 does not vary even in the occurrence of the crack 121 through which the first inspection gas reaches the reference electrode 104. The output current value of the oxygen sensor 50 in the atmosphere of the first inspection gas is kept at the same level (as indicated by line a) irrespective of the occurrence or nonoccurrence of the crack 121. However, the oxygen concentration of the reference electrode 104 becomes lowered in the occurrence of the crack 121 through which the second inspection gas reaches the reference electrode 104 as the oxygen concentration of the second inspection gas is lower than that of the first inspection gas and that of the reference gas. The oxygen ion conduction amount decreases with the oxygen concentration of the reference electrode 104. As a result, the output current value of the oxygen sensor 50 in the atmosphere of the second inspection gas (indicated by line c) becomes smaller than the output current value of the oxygen sensor 50 in the atmosphere of the first inspection gas (indicated by line a) as shown in FIG. 4.

Figure 5:
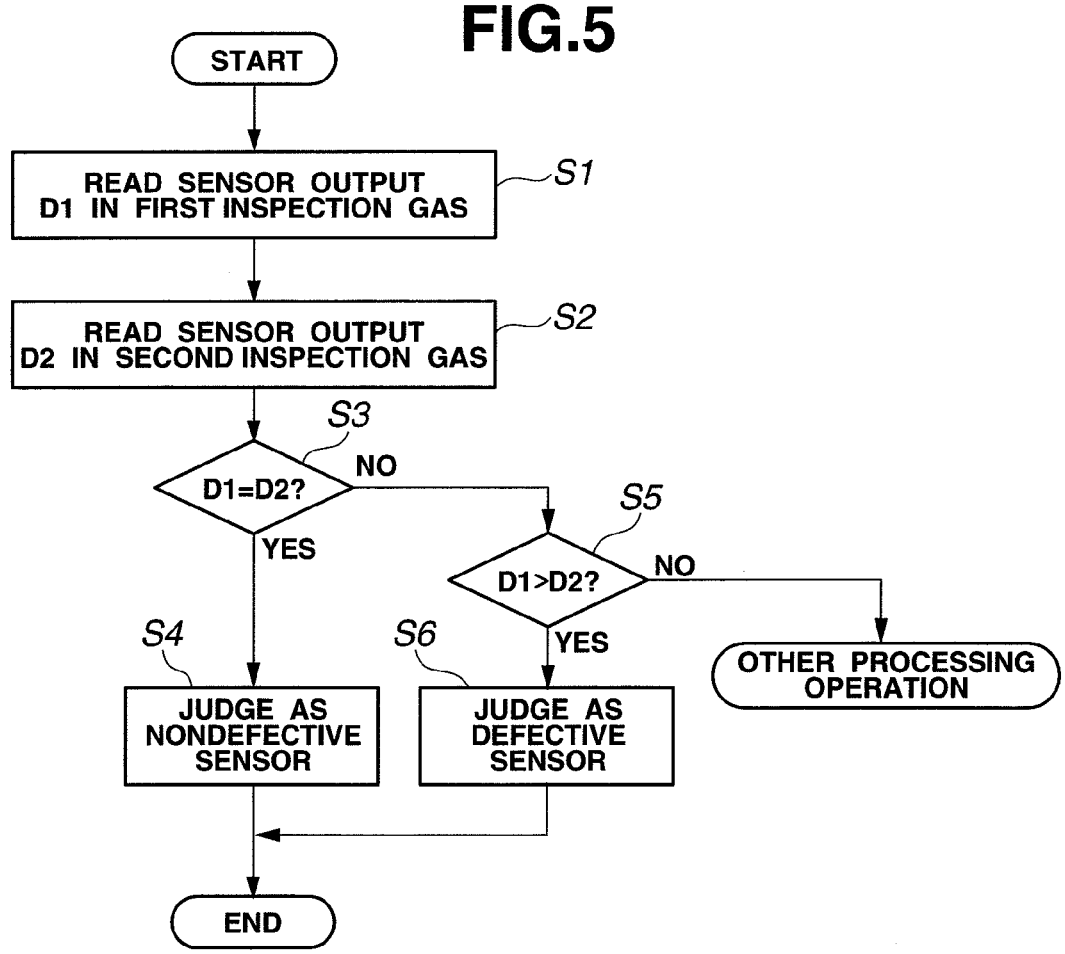
FIG. 5 is a flow chart for a sensor inspection program of the oxygen sensor inspection apparatus according to one embodiment of the present invention.

In the present embodiment, the quality inspection test is performed through a sensor inspection program of FIG. 5.

At step S1, the control unit 4 causes the gas supply unit 2 to supply the first inspection gas to the gas chamber 10*a* and reads a first output value D1 of the oxygen sensor 50 under the condition that the sensing portion 120 is subjected to the first inspection gas in the gas chamber 10*a*. More specifically, the control unit 4 controls the switching valve 13 to establish a communication between the first gas cylinder 11 and the gas chamber 10*a* and thereby supply the first inspection gas from the first gas cylinder 11 to the gas chamber 10*a* through the first and third gas pipes 15 and 18 and drain the existing gas out of the gas chamber 10*a* through the second gas pipe 17. After the lapse of a predetermined time from the initiation of control of the switching valve 13 (i.e. the initiation of the supply of the first inspection gas), the inside of the gas chamber 10*a* is filled with the first inspection gas so that the sensor element 51 including the sensing portion 120 is subjected to the first inspection gas in the gas chamber 10*a*. In this state, the control unit 4 causes the power supply unit 3 to apply and increase an inspection voltage between the reference electrode 104 and the sensing electrode 105 and thereby allow oxygen ion conduction from the reference electrode 104 to the sensing electrode 105. As the inspection voltage increases, the oxygen supply of the reference gas from the porous layer 103 to the reference electrode 104 reaches an upper limit so that the current between the reference electrode 104 and the sensing electrode 105 becomes saturated at a constant limiting current value. The control unit 4 reads this limiting current as the first output value D1 through the power supply unit 3 and stores the first output value D1 in the RAM.

At step S2, the control unit 4 causes the gas supply unit 2 to supply the second inspection gas to the gas chamber 10*a* and reads a second output value D1 of the oxygen sensor 50 under the condition that the sensing portion 120 is subjected to the second inspection gas in the gas chamber 10*a*. More specifically, the control unit 4 controls the switching valve 13 to establish a communication between the second gas cylinder 12 and the gas chamber 10*a* and thereby supply the second inspection gas from the second gas cylinder 12 to the gas chamber 10*a* through the first and fourth gas pipes 15 and 19 and drain the existing gas (first inspection gas) out of the gas chamber 10*a* through the second gas pipe 17. After the lapse of a predetermined time from the initiation of control of the switching valve 13 (i.e. the initiation of the supply of the second inspection gas), the inside of the gas chamber 10*a* is filled with the second inspection gas so that the sensor element 51 including the sensing portion 120 is subjected to the second inspection gas in the gas chamber 10*a*. In this state, the control unit 4 causes the power supply unit 3 to apply and increase an inspection voltage between the reference electrode 104 and the sensing electrode 105 and thereby allow oxygen ion conduction from the reference electrode 104 to the sensing electrode 105. When the inspection voltage increases so that the current between the reference electrode 104 and the sensing electrode 105 becomes saturated at a constant limiting current value, the control unit 4 reads the limiting current as the second output value D2 through the power supply unit 3 and stores the second output value D2 in the RAM.

At step S3, the control unit 4 retrieves the first and second sensor output values D1 and D2 from the RAM and determines whether the first sensor output value D1 is equal to the second sensor output value D2. Alternatively, the control unit 4 may determine whether the first sensor output value D1 is substantially equal to the second sensor output value D2 in such a manner that the difference between the sensor output values D1 and D2 falls within a given range. If Yes at step S3 (D1=D2), the program proceeds to step S4. If No at step S4 (D1≠D2), the program proceeds to step S5.

At step S4, the control unit 4 judges the oxygen sensor 50 as a nondefective (conforming) product.

At step S5, the control unit 4 determines whether the first sensor output value D1 is smaller than the second sensor output value D2. If Yes at step S5 (D1>D2), the program proceeds to step S6. If No at step S5 (D1<D2), the program proceeds to step S7.

At step S6, the control unit 4 judges the oxygen sensor 50 as a defective (nonconforming) product.

At step S7, the control unit 4 carries out the other processing operation such as error handling.

In this way, the oxygen sensor inspection apparatus 1 inspects the occurrence or nonoccurrence of the crack 121 in the oxygen sensor 50 and judges the oxygen sensor 50 as either a nondefective product or a defective product by comparison between the first and second output values D1 and D2 of the oxygen sensor 50.

Conventionally, the occurrence of a defect in the oxygen sensor 50 has been inspected by visual inspection called "red check test". The red check test goes through the steps of adhering a liquid penetrant to the sensing portion 120, removing excess liquid, applying a developer to draw the penetrant out of the defect to thereby show the location, shape and size of the defect. As already mentioned above, there is a possibility that a small crack may not be detected in such a visual inspection test. Further, the red check test requires a post-treatment process to burn out and remove the liquid penetrant from the sensing portion 120 when the oxygen sensor 50 is judged as a nondefective product. It however takes much time and effort to remove the liquid penetrant by the post-treatment process. In addition, the red check test is conducted before the fixing of the protector 57. If the sensor element 51 becomes cracked due to contact between the sensor element 51 and the protector 57 during the fixing of the protector 57, this subsequently developed crack cannot be checked by the red check test.

In the present embodiment, by contrast, the occurrence of a defect in the oxygen sensor 50 is judged based on the first and second output values D1 and D2 of the oxygen sensor 50 as described above. There are no need to use a liquid penetrant and no need to conduct a post-treatment process to remove the liquid penetrant. It is therefore possible in the present embodiment to obtain higher quality inspection accuracy than the conventional visual inspection (red check) test and to reduce the time and effort required for the quality inspection of the oxygen sensor 50. It is further possible to check even a defect occurring during the fixing of the protector 57 as the quality inspection test is conducted after the protector fixing process in the present embodiment.

Further, the limiting current between the reference electrode 104 and the sensing electrode 105 is measured as each of the first and second sensor output values D1 and D2 through the application of the increasing voltage. The limiting current between the reference electrode 104 and the sensing electrode 105 is in a proportional relationship with the oxygen concentrations of the sensor electrodes 104 and 105. The oxygen sensor 50 is judged to be defective when the second sensor output value D2 is lower than the first sensor output value D1. It is thus possible to inspect the oxygen sensor 50 easily and accurately by such electrical inspection test based on the limiting current measurement without the need to disassemble the oxygen sensor 50.

It is preferable that the oxygen amount of the first inspection gas and the oxygen amount of the atmospheric air do not change under the influence of the second inspection gas during the quality inspection test. If the second inspection gas reacts with oxygen in the first inspection gas or in the atmospheric air, the limiting current between the reference electrode 104 and the sensing electrode 105 varies in response to the change in the oxygen concentration of the first inspection gas or the atmospheric air. This results in a deterioration of inspection test accuracy. It is however possible in the present embodiment to inspect the oxygen sensor 50 easily and accurately by selecting the second inspection gas from the group consisting of nitrogen gas and inert gases such as helium gas, neon gas and argon gas, each of which is easy to handle and is inert to oxygen and does not react with oxygen in the first inspection gas or the atmospheric air.

The entire contents of Japanese Patent Application No. 2007-266462 (filed on Oct. 12, 2007) are herein incorporated by reference.

Although the present invention has been described with reference to the above-specific embodiment of the invention, the invention is not limited to this exemplary embodiment. Various modification and variation of the embodiment described above will occur to those skilled in the art in light of the above teachings. For example, the oxygen sensor 50 can be of any other type such as limiting-current type (plane form etc.). The scope of the invention is defined with reference to the following claims.

What is claimed is:

1. An inspection method of an oxygen sensor, the oxygen sensor comprising a sensing portion having a reference electrode, a sensing electrode and an oxygen ion conducting solid electrolyte layer arranged between the reference electrode and the sensing electrode, the inspection method comprising:
    reading a first output value of the oxygen sensor under a condition that the sensing portion of the oxygen sensor is subjected to a first inspection gas and then a second output value of the oxygen sensor under a condition that the sensing portion of the oxygen sensor is subjected to a second inspection gas, the first and second inspection gases having different oxygen concentrations from each other; and
    judging the oxygen sensor to be defective or nondefective based on the first and second output values.

2. The inspection method according to claim 1, wherein each of the first and second output values is a limiting current between the reference electrode and the sensing electrode as measured by applying an increasing voltage between the reference electrode and the sensing electrode to allow oxygen ion conduction from the reference electrode to the sensing electrode.

3. The inspection method according to claim 2, wherein the oxygen concentration of the second inspection gas is lower than the oxygen concentration of the first inspection gas; and the oxygen sensor is judged to be defective when the second output value is smaller than the first output value.

4. The inspection method according to claim 1, wherein the first inspection gas is atmospheric air and the second inspection gas is gas inert to oxygen.

5. The inspection method according to claim 4, wherein the second inspection gas is either one of nitrogen gas, argon gas and helium gas.

6. A production method of an oxygen sensor, the oxygen sensor comprising a substrate portion, a sensing portion disposed on the substrate portion and having a reference electrode, a sensing electrode and an oxygen ion conducting solid electrolyte layer arranged between the reference electrode and the sensing electrode and a protector covering therewith the sensing portion, the production method comprising:
    printing the reference electrode, the solid electrolyte layer and the sensing electrode successively on the substrate portion;
    sintering the printed reference electrode, solid electrolyte layer and sensing electrode to form the sensing portion on the substrate portion;
    after said sintering, fixing the protector to cover the sensing portion with the protector;
    after said fixing, reading a first output value of the oxygen sensor under a condition that the sensing portion of the oxygen sensor is subjected to a first inspection gas and then a second output value of the oxygen sensor under a condition that the sensing portion of the oxygen sensor is subjected to a second inspection gas, the first and second inspection gases having different oxygen concentrations from each other; and
    judging the oxygen sensor to be defective or nondefective based on the first and second output values.

7. An inspection apparatus of an oxygen sensor, the oxygen sensor comprising a sensing portion having a reference electrode, a sensing electrode and an oxygen ion conducting solid electrolyte layer arranged between the reference electrode and the sensing electrode, the inspection apparatus comprising:
    a gas supply unit that supplies first and second inspection gases selectively to the sensing portion, the first and second inspection gases having different oxygen concentrations from each other; and
    a control unit that reads a first output value of the oxygen sensor under a condition that the sensing portion of the oxygen sensor is subjected to the first inspection gas and then a second output value of the oxygen sensor under a condition that the sensing portion of the oxygen sensor is subjected to the second inspection gas and judges the oxygen sensor to be defective or nondefective based on the first and second output values.

* * * * *